United States Patent
Hargreaves et al.

(10) Patent No.: US 7,230,108 B2
(45) Date of Patent: Jun. 12, 2007

(54) QUINOLINE DERIVATIVES AS GLUCOKINASE LIGANDS

(75) Inventors: Rodney Brian Hargreaves, Macclesfield (GB); Christopher Daniel Davies, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/534,651

(22) PCT Filed: Nov. 13, 2003

(86) PCT No.: PCT/GB03/04915

§ 371 (c)(1),
(2), (4) Date: May 12, 2005

(87) PCT Pub. No.: WO2004/045614

PCT Pub. Date: Jun. 3, 2004

(65) Prior Publication Data

US 2006/0079553 A1    Apr. 13, 2006

(30) Foreign Application Priority Data

Nov. 19, 2002 (GB) ................................ 0226931.4

(51) Int. Cl.
C07D 215/38 (2006.01)
A61K 31/47 (2006.01)

(52) U.S. Cl. ........................ 546/169; 514/314
(58) Field of Classification Search ............. 546/169; 514/314
See application file for complete search history.

(56) References Cited

U.S. PATENT DOCUMENTS

| 4,146,631 A | 3/1979 | Ford et al. ............. 514/381 |
| 6,448,399 B1 * | 9/2002 | Corbett et al. .......... 544/183 |
| 6,545,155 B2 * | 4/2003 | Corbett et al. .......... 546/159 |
| 6,613,942 B1 | 9/2003 | Ling et al. |
| 2004/0214868 A1 | 10/2004 | Hayter et al. |
| 2005/0054715 A1 | 3/2005 | Hayter et al. |
| 2005/0080106 A1 | 4/2005 | Boyd et al. |
| 2006/0058353 A1 | 3/2006 | Mckerrecher et al. |

FOREIGN PATENT DOCUMENTS

| EP | 1336607 A1 | 8/2003 |
| EP | 1600442 | 11/2005 |
| GB | 2385328 A | 8/2003 |
| JP | 08 173525 | 7/1996 |
| JP | 08 301760 | 11/1996 |
| JP | 09040557 A | 2/1997 |
| JP | 2000086657 A | 3/2000 |
| WO | WO-00/26202 A | 5/2000 |
| WO | WO-00/26202 A1 | 5/2000 |
| WO | WO-00/58293 A | 10/2000 |
| WO | WO-00/58293 A1 | 10/2000 |
| WO | WO 01/19788 | 3/2001 |
| WO | WO-01/20327 A1 | 3/2001 |
| WO | WO-01/44216 A1 | 6/2001 |
| WO | WO-01/83465 A2 | 11/2001 |
| WO | WO-01/83478 A2 | 11/2001 |
| WO | WO-01/85706 A1 | 11/2001 |
| WO | WO-01/85707 A1 | 11/2001 |
| WO | WO-02/00633 A1 | 1/2002 |
| WO | WO-02/08209 A1 | 1/2002 |
| WO | WO-02/14312 A1 | 2/2002 |
| WO | WO 02/24682 * | 3/2002 |
| WO | WO-02/24682 A | 3/2002 |
| WO | WO-02/24682 A1 | 3/2002 |
| WO | WO-02/46173 A | 6/2002 |
| WO | WO-02/46173 A1 | 6/2002 |
| WO | WO-02/48106 A2 | 6/2002 |
| WO | WO-02/064545 A1 | 8/2002 |
| WO | WO-03/000262 A1 | 1/2003 |
| WO | WO-03/000267 A1 | 1/2003 |

(Continued)

OTHER PUBLICATIONS

Kar, "Cinchophen Analogues as Potential CNS Agents," Journal of Pharmaceutical Sciences, American Pharmaceutical Association 72(9):1082-1084 (1983).

Mein, Database Crossfile Beilstein 'Online! Beilstein Institut Zur Foerderung Der Chemischen Wissenshaften, Database accession No. 6511458(BRN) XP002272206 abstract and Indian J. Chem. Sect., 25(9):886 (1986).

Kudri, "Enamine Product Listing," Database Chemcats 'Online! Chemical Abstract Service, XP002272448 Order No. T0505-1260, T0504-9244 (2001).

(Continued)

*Primary Examiner*—D. Margaret Seaman
(74) *Attorney, Agent, or Firm*—Morgan Lewis & Bockius LLP

(57) ABSTRACT

Compounds of formula (I), wherein one of $R^1$ and $R^2$ is selected from a group (IA), ring A is substituted pyridin-z-yl of thiazol-z-yl, the other substituents are as described in the description and their use in the treatment or prevention of a disease or medical conditions mediated through glucokinase

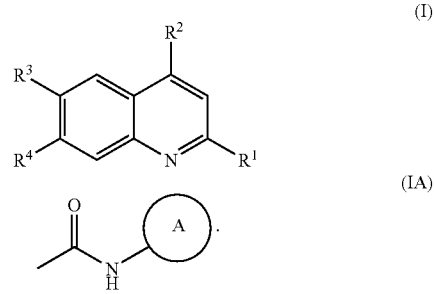

10 Claims, No Drawings

FOREIGN PATENT DOCUMENTS

| | | |
|---|---|---|
| WO | WO-03/015774 A1 | 2/2003 |
| WO | WO-03/022856 A1 | 3/2003 |
| WO | WO-03/028641 A2 | 4/2003 |
| WO | WO-03/047626 A1 | 6/2003 |
| WO | WO-03/048152 A2 | 6/2003 |
| WO | WO-03/055482 A1 | 7/2003 |
| WO | WO-03/080585 A1 | 10/2003 |
| WO | WO-03/082838 A | 10/2003 |
| WO | WO-03/082838 A1 | 10/2003 |
| WO | WO-03/095438 A1 | 11/2003 |
| WO | WO-03/097824 A1 | 11/2003 |
| WO | WO-04/002481 A1 | 1/2004 |
| WO | WO 2004/031179 | 4/2004 |
| WO | WO-04/045614 A1 | 6/2004 |
| WO | WO-04/046139 A1 | 6/2004 |
| WO | WO-04/050645 A1 | 6/2004 |
| WO | WO-04/052869 A1 | 6/2004 |
| WO | WO-04/063179 A1 | 7/2004 |
| WO | WO-04/063194 A1 | 7/2004 |
| WO | WO-04/072031 A2 | 8/2004 |
| WO | WO-04/072066 A1 | 8/2004 |
| WO | WO-04/076420 A1 | 9/2004 |
| WO | WO-04/081001 A1 | 9/2004 |
| WO | WO 2004/076420 | 9/2004 |
| WO | WO-04/110375 A2 | 12/2004 |
| WO | WO-05/044801 A1 | 5/2005 |
| WO | WO-05/049019 A1 | 6/2005 |
| WO | WO-05/054200 A1 | 6/2005 |
| WO | WO-05/054233 A1 | 6/2005 |
| WO | WO-05/056530 A1 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |

OTHER PUBLICATIONS

Kennedy, "Interchim Intermediated," Database Chemcats 'Online! Chemical Abstracts Service XP002272449 (2002).

Edmont et al., "Synthesis and evaluation of quinoline carboxyguanidines as antidiabetic agents," Bioorganic & Medicinal Chemistry Letters 10(16):1831-1834 (2000).

Alvarez et al., "Evidence that Glucokinase Regulatory Protein is Expressed and Interacts with Glucokinase in Rat Brain," Journal of Neurochemistry 80:45-53 (2002).

Alvarez et al., "Expression of the Glucagon-Like Peptide-1 Receptor Gene in Rat Brain," Journal of Neurochemistry 66(3):920-927 (1996).

Bell et al., "Glucokinae Mutations, Insulin Secretion, and Diabetes Mellitus," Annu. Rev. Physiol. 58:171-186 (1996).

Brocklehurst et al., "Stimulation of Hepatocyte Glucose Metabolism by Novel Small Molecule Glucokinase Activators," Diabetes 53:535-541 (2004).

Caro et al., "Liver Glucokinase: Decreased Activity in Patients with Type II Diabetes," Horm. Metab. Res. 27:19-22 (1995).

Christesen et al., "The Second Activating Glucokinase Mutation (A456V) Implications for Glucose Homeostasis and Diabetes Therapy," Diabetes 51:1240-1246 (2002).

Corbett, "Track 3—Mastering Medicinal Chemistry: Applying Organic Chemistry to Biological Problems, Success Stories in Medicinal Chemistry," Molecular Medicine Tri-Conference, Moscone West Convention Center, San Francisco California, Mar. 26, 2005—11:00-11:30 Glucokinase Activators: Discovery of Novel, Orally Active Glucse Lowering Agents, Mar. 24-26, 2004.

DeFronzo, "The Triumvirate: β-Cell, Muscle, Liver—A Collusion Responsible for NIDDM," Diabetes 37:667-687 (1988).

Desai et al., "Phenotypic correction of Diabetic Mice by Adenovirus-Mediated Glucokinase Expression," Diabetes 50:2287-2295 (2001).

Ferre et al., "Correction of Diabetic Alterations by Glucokinase," Proc. Natl. Acad. Sci. USA 93:7225-7230 (1996).

Froguel et al., "Familial Hyperglycemia Due to Mutations in Glucokinase—Definition of a Subtype of Diabetes Mellitus," The New England Journal of Medicine 328(10):697-702 (1993).

Fujimoto et al., "Administration of D-Glucosamine into the Third Cerebroventricle Induced Feeding Accompanied by Hyperglycemia in Rats," Life Sciences 37(26):2475-2482 (1985).

Glaser et al., "Familial Hyperinsulinism Caused by an Activating Glucokinase Mutation," The New England Journal of Medicine 338(4):226-230 (1998).

Grimsby et al., "Allosteric Activators of Glucokinase: Potential Role in Diabetes Therapy," Science 301:370-373 (2003).

Grimsby, "Glucokinase Activators—Potential Treatment for Type 2 Diabetes," Roche—SMi Diabetes London UK pp. 28-29 (2002.

Kurata et al., "D-Glucose Suppression of Eating After Intra-Third Ventricle Infusion in Rat," Physiology & Behavior 37:615-620 (1986).

Kurata et al., "Structural Evaluation of Glucose Analogues on Feeding Elicitation in Rat," Metabolism 38(1):46-51 (1989).

Levin et al., "Brain Glucose Sensing and body Energy Homeostasis: Role in Obesity and Diabetes," A.J. of Physiology 276:R1223-R1231 (1999).

Levin et al., "Differential Effects of Diet and Obesity on High and Low Affinity Sulfonylurea Binding Sites in the Rat Brain," Brain Research 739:293-300 (1996).

Levin et al., "In vivo and In vitro Regulation of [$^3$H] Glyburide Binding to Brain Sulfonylurea Receptors in Obesity-Prone and Resistant Rats by Glucose," Brain Research 776:146-153 (1997).

Levin et al., "Reduced Glucose-Induced Neuronal Activation in the Hypothalamus of Diet-Induced Obese Rats," Brain Research 808:317-319 (1998).

Levin, "Glucosensing Neurons do More Than Just Sense Glucose," International Journal of Obesity 25(5):S68-S72 (2001).

Lynch et al., "Localization of Glucokinase Gene Expression in the Rat Brain," Diabetes 49:693-700 (2000).

McKerrecher et al., "Discovery, Synthesis and Biological Evaluation of Novel Glucokinase Activators," Bioorganic & Medicinal chemistry Letters 15:2103-2106 (2005).

Mobbs et al., "Brain Glucose-Sensing Mechanisms: Ubiquitous Silencing by Aglycemia vs. Hypothalamic Neuroendocrine Responses," Am. J. Physiol. Endocrinol. Metab. 281:E649-E654 (2001).

Moore et al., "Acute Fructose Administration Improves Oral Glucose Tolerance in Adults with Type 2 Diabetes," Diabetes Care 24(11):1882-1887 (2001).

Printz et al., "Mammalian Glucokinase," Annu. Rev. Nutr. 13:463-496 (1993).

Qian-Cutrone et al., "Glucolipsin A and B, Two New Glucokinase Activators Producted by *Streptomyces purpurogenischeroticus* and *Nocardia vaccinii*," The Journal of Antibiotics 52(3):245-255 (1999).

Roncero et al., "Functional Glucokinase Isoforms are Expressed in Rat Brain," Journal of Neurochemistry 74(5):1848-1857 (2000).

Rowe et al., "Potassium Channel Dysfunction in Hypothalamic Glucose-Receptive Neurones of Obese Zucker Rats," Journal of Physiology 497(2):365-377 (1996).

Schuit et al., "Perspectives in Diabetes—Glucose Sensing in Pancreatic β-Cells—A Model for the Study of Other Glucose-Regulated Cells in Gut, Pancreas, and Hypothalamus," Diabetes 50:1-11 (2001).

Seoane et al., "Glucokinase Overexpression Restores Glucoes Utilization and Storage in Cultured Hepatocytes from Male Zucker Diabetic Fatty Rats," The Journal of Biological Chemistry 274(45):31833-31838 (1999).

Shiota et al., "Glucokinase Gene Locus Transgenic Mice are Resistant to the Development of Obesity-Induced Type 2 Diabetes," Diabetes 50:622-629 (2001).

Spanswick et al., "Insulin Activates ATP-Sensitive $K^+$ Channels in Hypothalamic Neurons of Lean, but Not Obese Rats," Nature Neuroscience 3(8):757-758 (2000).

Spanswick et al., "Leptin Inhibits Hypothalamic Neurons by Activation of ATP-Sensitive Potassium Channels," Nature 390:521-525 (1997).

Velho et al., "Impaired Hepatic Glycogen Synthesis in Glucokinase-Deficient (MODY-2) Subjects," J. Clin. Invest. 98:1755-1761 (1996).

Yang et al., "Hypothalamic Glucose Sensor—Similarities to an dDifferenes from Pancreatic β-Cell Mechanisms," Diabetes 48:1763-1772 (1999).

Carroll et al., "Stress, Signalling and Control," Biochemical Society Meeting 679 Jul. 2-4, 2003.

U.S. Appl. No. 10/578,021, filed Apr. 28, 2006, Peter William Rodney Caulkett et al., WO 2005/044801, May 19, 2005.

U.S. Appl. No. 10/579,337, filed May 15, 2006, Craig Johnstone et al., WO 2005/054200, Jun. 16, 2005.

U.S. Appl. No. 10/579,552, filed May 16, 2006, Craig Johnstone et al., WO 2005/054233, Jun. 16, 2005.

Anderson et al "Pyridopyrimidines. 6. Nucleophilic substitutions in the Pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn., 55:2504-2507 (1982).

Coghlan "Small molecule Glucokinase Activators (GKAs) as novel anti-diabetic agents" Society for Medicines Research Seminar (Jun. 2004).

Coghlan "Small molecule Glucokinase Activators (GKAs) as novel anti-diabetic agents" CIDEM seminar (May 2005).

Gill et al. "Stimulation of insulin release by a small molecule glucokinase activator" EASD Islet Study Group Abstract (Nov. 2005).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Leighton et al. "Small molecule glucokinase activators as novel anti-diabetic agents" Biochem Soc Trans. 33(Pt 2):371-374 (Apr. 2005).

McKerrecher "Design and synthesis of novel glucokinase activators" 13th RSC-SCI Medicinal Chemistry Symposium, Churchill College Cambridge (Sep. 2005).

McKerrecher et al. "Design and synthesis of novel glucokinase activators as potential treatment for type 2 diabetes" Frontiers in Medicinal Chemistry, Frankfurt (Mar. 2006).

McKerrecher et al. "Design of a potent, soluble glucokinase activator with excellent in vivo efficacy" Bioorg Med Chem Lett. 16(10):2705-2709 (May 15, 2006) Epub Feb. 28, 2006.

McKerrecher et al. "Identification of orally bioavailable small molecule activators of glucokinase" Abstract, Anglo-Swedish Medicinal Chemistry Meeting (Mar. 2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, Anaheim, California, Mar. 28-Apr. 1, 2004 (paper 341).

Sekera et al. "No. 69.—Recherches sur les anesthesiques locaux (XI memoire) Synthese de quelques nouveaux β-alcoxyethoxycarbanilates et β-alcoxyethoxycinchonamides amines" Bull Chem Soc France 401-404 (1959) (Translation enclosed).

Vertigan et al. "Impact of cell glycogen content on modulation of hepatocyte glucose metabolism by pharmacological agents" Diabetologia, vol. 47 Supp 1, A214, 589 (2004).

* cited by examiner

QUINOLINE DERIVATIVES AS GLUCOKINASE LIGANDS

RELATED APPLICATIONS

This application is a national stage filing under 35 U.S.C. 371 of International Application PCT/GB2003/004915, filed Nov. 13, 2003, which claims priority from United Kingdom Application No. 0226931.4, filed Nov. 19, 2002, the specifications of each of which are incorporated by reference herein. International Application PCT/GB2003/004915 was published under PCT Article 21(2) in English.

The present invention relates to chemical compounds useful in the treatment or prevention of a disease or medical conditions mediated through glucokinase (GLK), leading to a decreased glucose threshold for insulin secretion. In addition the compounds are predicted to lower blood glucose by increasing hepatic glucose uptake. Such compounds may have utility in the treatment of type 2 diabetes and obesity. The invention also relates to processes for preparing said compounds, pharmaceutical compositions comprising said compounds, and the use of such a compound in the conditions described above.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6–10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, type 2 maturity-onset diabetes of the young (MODY-2), the diabetes is caused by GLK loss of function mutations [3, 4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9–12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is elevated in the post-absorptive state whereas F1P predominates in the post-prandial state. In contrast to the hepatocyte, the pancreatic β-cell expresses GLK in the absence of GLKRP. Therefore, β-cell GLK activity is regulated exclusively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act exclusively in the liver. However, compounds with either profile are predicted to be of therapeutic benefit in treating type 2 diabetes as this disease is characterised by defective glucose utilisation in both tissues.

GLK and GLKRP and the $K_{ATP}$ channel are expressed in neurones of the hypothalamus, a region of the brain that is important in the regulation of energy balance and the control of food intake [14–18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23–28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "diabesity" target (of benefit in both Diabetes and Obesity).

In WO 00/58293 and WO 01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described below. Compounds of the present invention may activate GLK directly or may activate GLK by inhibiting the interaction of GLKRP with GLK. Many compounds of the present invention may show favourable selectivity compared to known GLK activators.

International application number: WO03/000267 describes a group of benzoyl amino pyridyl carboxylic acids which are activators of the enzyme glucokinase (GLK), International application number WO03/015774 describes a group of benzoylamino heterocycle compounds as glucokinase activators and International application number WO03/000262 describes a group or vinyl phenyl derivatives as glucokinase activators.

According to the present invention there is provided a compound of formula (I):

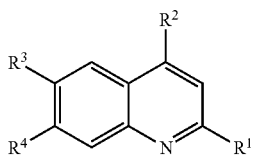

wherein:
One of R¹ and R² is selected from a group (IA):

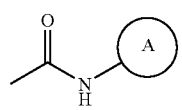

and the other R¹ or R² is selected from hydrogen, $C_{1-4}$alkyl, $C_{1-4}$alkoxy, carbocyclyl, heterocyclyl, carbocyclyloxy and heterocyclyloxy; wherein this R¹ or R² may be optionally substituted on carbon by one or more groups selected from R⁵; and wherein if said heterocyclyl contains an —NH— moiety that nitrogen may be optionally substituted by $C_{1-4}$alkyl;

Ring A is pyridin-2-yl or thiazol-2-yl; wherein said pyridin-2-yl or thiazol-2-yl may be optionally substituted on carbon by one or more groups selected from R⁶;

one of R³ and R⁴ is hydrogen and the other is selected from hydrogen, $C_{1-4}$alkyl, $C_{1-4}$alkoxy, carbocyclyl, heterocyclyl, carbocyclyloxy and heterocyclyloxy; wherein R³ and R⁴ may be independently optionally substituted on carbon by one or more groups selected from R⁷; and wherein if said heterocyclyl contains an —NH— moiety that nitrogen may be optionally substituted by $C_{1-4}$alkyl;

R⁶ is selected from halo, carboxy and $C_{1-4}$alkyl;

R⁵ and R⁷ are independently selected from halo, $C_{1-4}$alkyl, $C_{1-4}$alkoxy, N-($C_{1-4}$alkyl)amino, N,N-($C_{1-4}$alkyl)₂ amino, carbocyclyl, heterocyclyl, carbocyclyloxy, heterocyclyloxy and carbocyclylidenyl; wherein R⁵ and R⁷ may be independently optionally substituted on carbon by one or more R⁸; and wherein if said heterocyclyl contains an —NH— moiety that nitrogen may be optionally substituted by $C_{1-4}$alkyl;

R⁸ is selected from halo, carboxy, methyl, ethyl, methoxy, ethoxy, methylamino, ethylamino, dimethylamino, diethylamino and N-methyl-N-ethylamino; or a salt, solvate or pro-drug thereof.

Compounds of formula (I) may form salts which are within the ambit of the invention. Pharmaceutically acceptable salts are preferred although other salts may be useful in, for example, isolating or purifying compounds.

The term "halo" includes chloro, bromo, fluoro and iodo; preferably chloro, bromo and fluoro; most preferably fluoro.

In this specification the term "alkyl" includes both straight and branched chain alkyl groups. For example, "$C_{1-6}$alkyl" and "$C_{1-4}$alkyl" includes propyl, isopropyl and t-butyl.

A "carbocyclyl" is a saturated, partially saturated or unsaturated, mono or bicyclic carbon ring that contains 3–12 atoms; wherein a —CH₂— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclohexyl or phenyl. Most particularly phenyl.

A "heterocyclyl" is a saturated, partially saturated or unsaturated, monocyclic or bicyclic ring containing 3–12 atoms of which at least one atom is chosen from nitrogen, sulphur or oxygen, wherein a —CH₂— group can optionally be replaced by a —C(O)— or sulphur atoms in a heterocyclic ring may be oxidised to S(O) or S(O)₂. A 'heterocyclyl' ring may, unless otherwise specified, be carbon or nitrogen linked, unless linking via nitrogen leads to a quaternary nitrogen. Preferably a "heterocyclyl" is a saturated, partially saturated or unsaturated, monocyclic or bicyclic ring wherein each ring contains 5 or 6 atoms of which 1 to 3 atoms are nitrogen, sulphur or oxygen, which may, unless otherwise specified, be carbon or nitrogen linked, wherein a —CH₂— group can optionally be replaced by a —C(O)— or sulphur atoms in a heterocyclic ring may be oxidised to S(O) or S(O)₂ groups. Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, isoxazolyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiazolyl, thiadiazolyl, isothiazolyl, 1,2,4-triazolyl, 1,2,3-triazolyl, pyranyl, indolyl, pyrimidyl, thiazolyl, pyrazinyl, pyridazinyl, pyridyl, 4-pyridonyl, quinolyl and 1-isoquinolonyl. Preferably the term "heterocyclyl" refers to monocyclic heterocyclic rings with 5- or 6-membered systems, such as isoxazolyl, pyrrolidinyl, 2-pyrrolidonyl, 2,5-dioxopyrrolidinyl, morpholino, tetrahydrofuranyl, piperidyl, piperazinyl, thiomorpholino, tetrahydropyranyl, thienyl, imidazolyl, 1,2,4-triazolyl, 1,3,4-triazolyl, indolyl, thiazolyl, thiadiazolyl, pyrazinyl, pyridazinyl and pyridyl. Preferred examples of 5/6 and 6/6 bicyclic ring systems include benzofuranyl, benzimidazolyl, benzthiophenyl, benzthiazolyl, benzisothiazolyl, benzoxazolyl, benzisoxazolyl, pyridoimidazolyl, pyrimidoimidazolyl, quinolinyl, isoquinolinyl, quinoxalinyl, quinazolinyl, phthalazinyl, cinnolinyl and naphthyridinyl.

Examples of $C_{1-4}$alkyl and $C_{1-6}$alkyl include methyl, ethyl, propyl, isopropyl, sec-butyl and tert-butyl; examples of $C_{1-4}$alkoxy include methoxy, ethoxy, propoxy and tert-butoxy; examples of N-($C_{1-4}$alkyl)amino include methylamino, ethylamino and isopropylamino; examples of N,N-($C_{1-4}$alkyl)₂amino include dimethylamino, N-methyl-N-ethylamino and N-ethyl-N-isopropylamino; examples of carbocyclylidenyl are cyclopentylidenyl and 2,4-cyclohexadien-1-ylidenyl.

It is to be understood that, insofar as certain of the compounds of formula (I) defined below may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

Suitable compounds of formula (I) are those wherein any one or more of the following apply. Such values may be used where appropriate with any of the definitions, claims or embodiments defined hereinbefore or hereinafter.

$R^1$ is selected from a group (IA) (as depicted above).

$R^2$ is selected from a group (IA) (as depicted above).

One of $R^1$ and $R^2$ is selected from a group (IA) (as depicted above) and the other $R^1$ or $R^2$ is selected from $C_{1-4}$alkoxy; wherein this $R^1$ or $R^2$ may be optionally substituted on carbon by one or more groups selected from $R^5$.

One of $R^1$ and $R^2$ is selected from a group (IA) (as depicted above) and the other $R^1$ or $R^2$ is selected from $C_{1-4}$alkoxy; wherein Ring A is optionally substituted by carboxy and the $C_{1-4}$alkoxy group is substituted on carbon by one or more groups selected from $R^5$.

One of $R^1$ and $R^2$ is selected from a group (A) (as depicted above) and the other $R^1$ or $R^2$ is selected from $C_{1-4}$alkoxy, carbocyclyloxy; wherein this $R^1$ or $R^2$ may be optionally substituted on carbon by one or more groups selected from $R^5$
wherein: $R^5$ is selected from halo, carbocyclyl or carbocyclylidenyl; wherein $R^5$ may be optionally substituted on carbon by one or more $R^8$ wherein: $R^8$ is selected from halo and methyl.

One of $R^1$ and $R^2$ is selected from a group (IA) (as depicted above) and the other $R^1$ or $R^2$ is selected from $C_{1-4}$alkoxy; wherein this $R^1$ or $R^2$ may be optionally substituted on carbon by one or more groups selected from $R^5$
wherein: $R^5$ is selected from carbocyclyl; wherein $R^5$ may be optionally substituted on carbon by one or more $R^8$ wherein:
$R^8$ is selected from halo and methyl.

One of $R^1$ and $R^2$ is selected from a group (IA) (as depicted above) and the other $R^1$ or $R^2$ is selected from methoxy, ethoxy, sec-butoxy, phenoxy, benzocyclopentyloxy; wherein this $R^1$ or $R^2$ may be optionally substituted on carbon by one or more groups selected from $R^5$
wherein: $R^5$ is selected from fluoro, phenyl and cyclopenylidenyl; wherein $R^5$ may be optionally substituted on carbon by one or more $R^8$ wherein:
$R^8$ is selected from chloro and methyl.

One of $R^1$ and $R^2$ is selected from a group (IA) (as depicted above) and the other $R^1$ or $R^2$ is selected from methoxy and sec-butoxy; wherein this $R^1$ or $R^2$ may be optionally substituted on carbon by one or more groups selected from $R^5$
wherein: $R^5$ is selected from phenyl; wherein $R^5$ may be optionally substituted on carbon by one or more $R^8$ wherein: $R^8$ is selected from chloro and methyl.

One of $R^1$ and $R^2$ is selected from a group (IA) (as depicted above) and the other $R^1$ or $R^2$ is selected from 2-chlorobenzyloxy, 2-methylbenzyloxy, sec-butoxy, cyclopenylidenylmethoxy, 1-cyclopenylidenylethoxy, phenoxy, benzocyclopent-1-yloxy and 2-phenyl-2,2-difluoroethoxy.

One of $R^1$ and $R^2$ is selected from a group (IA) (as depicted above) and the other $R^1$ or $R^2$ is selected from 2-chlorobenzyloxy, 2-methylbenzyloxy and sec-butoxy.

Ring A is pyridin-2-yl optionally substituted on carbon by one or more groups selected from $R^6$.

Ring A is thiazol-2-yl optionally substituted on carbon by one or more groups selected from $R^6$.

Ring A is pyridin-2-yl or thiazol-2-yl; wherein said pyridin-2-yl or thiazol-2-yl may be optionally substituted on carbon by one or more groups selected from $R^6$ wherein: $R^6$ is carboxy.

Ring A is thiazol-2-yl, 5-carboxythiazol-2-yl, pyridin-2-yl or 5-carboxypyridin-2-yl.

Ring A is 5-carboxythiazol-2-yl or 5-carboxypyridin-2-yl.

One of $R^3$ and $R^4$ is hydrogen and the other is selected from hydrogen, $C_{1-4}$alkyl, $C_{1-4}$alkoxy and carbocyclyloxy; wherein $R^3$ and $R^4$ may be independently optionally substituted on carbon by one or more groups selected from $R^7$; wherein: $R^7$ is halo, carbocyclyl and carbocyclylidenyl.

One of $R^3$ and $R^4$ is hydrogen and the other is selected from hydrogen or $C_{1-4}$alkyl.

One of $R^3$ and $R^4$ is hydrogen and the other is selected from hydrogen, methyl, methoxy, ethoxy, phenoxy and benzocyclopentyloxy; wherein $R^3$ and $R^4$ may be independently optionally substituted on carbon by one or more groups selected from $R^7$;
wherein: $R^7$ is fluoro, phenyl and cyclopentylidenyl.

$R^3$ is hydrogen or $C_{1-4}$alkyl and $R^4$ is hydrogen.

One of $R^3$ and $R^4$ is hydrogen and the other is selected from hydrogen, methyl, cyclopenylidenylmethoxy, 1-cyclopenylidenylethoxy, phenoxy, benzocyclopent-1-yloxy and 2-phenyl-2,2-difluoroethoxy.

$R^3$ is hydrogen or methyl and $R^4$ is hydrogen.

$R^5$ is carbocyclyl, wherein $R^5$ may be optionally substituted on carbon by one or more $R^8$.

$R^5$ is phenyl wherein $R^5$ may be optionally substituted on carbon by one or more $R^8$
wherein: $R^8$ is selected from halo and methyl.

$R^6$ is carboxy.

$R^8$ is halo or $C_{1-4}$alkyl.

$R^8$ is $C_{1-4}$alkyl or chloro.

$R^8$ is methyl or chloro.

Therefore in a further aspect of the invention, there is provided a compound of formula (I) (as depicted above) wherein: One of $R^1$ and $R^2$ is selected from a group (IA) (as depicted above) and the other $R^1$ or $R^2$ is selected from $C_{1-4}$alkoxy; wherein this $R^1$ or $R^2$ may be optionally substituted on carbon by one or more groups selected from $R^5$ wherein:
$R^5$ is selected from carbocyclyl; wherein $R^5$ may be optionally substituted on carbon by one or more $R^8$ wherein:
$R^8$ is selected from halo and methyl; and
Ring A is pyridin-2-yl or thiazol-2-yl; wherein said pyridin-2-yl or thiazol-2-yl may be optionally substituted on carbon by one or more groups selected from $R^6$ wherein:
$R^6$ is carboxy; and
one of $R^3$ and $R^4$ is hydrogen and the other is selected from hydrogen or $C_{1-4}$alkyl; or a salt, solvate or pro-drug thereof.

Therefore in a further aspect of the invention, there is provided a compound of formula (I) (as depicted above) wherein One of $R^1$ and $R^2$ is selected from a group (IA) (as depicted above) and the other $R^1$ or $R^2$ is selected from 2-chlorobenzyloxy, 2-methylbenzyloxy and sec-butoxy;
Ring A is 5-carboxythiazol-2-yl or 5-carboxypyridin-2-yl; and
$R^3$ is hydrogen or methyl; and $R^4$ is hydrogen;

or a salt, solvate or pro-drug thereof.

In another aspect of the invention, preferred compounds of the invention include:

2-(2-Chlorobenzyloxy)-4-[N-(5-carboxythiazol-2-yl)carbamoyl]-6-methylquinoline;

2-(2-Chlorobenzyloxy)-4-[N-(5-carboxythiazol-2-yl)carbamoyl]-quinoline;

2-(2-Chlorobenzyloxy)4-[N-(5-carboxypyrid-2-yl)carbamoyl]-6-methylquinoline;

2-(2-Chlorobenzyloxy)4-[N-(5-carboxypyrid-2-yl)carbamoyl]-quinoline;

2-[N-(5-carboxypyrid-2-yl)carbamoyl]-4-(2-methylbenzyloxy)-quinoline; and 2-(1-methylpropoxy)4-[N-(5-carboxythiazol-2-yl)carbamoyl]-quinoline;

or a salt, solvate or pro-drug thereof.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in vivo hydrolysable ester). Various forms of pro-drugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen;

c) H. Bundgaard, Chapter 5 "Design and Application of Prodrugs", by H. Bundgaard p. 113–191 (1991);

d) H. Bundgaard, Advanced Drug Delivery Reviews, 8, 1–38 (1992);

e) H. Bundgaard, et al., Journal of Pharmaceutical Sciences, 77, 285 (1988); and f) N. Kakeya, et al., Chem Pharm Bull, 32, 692 (1984).

The contents of the above cited documents are incorporated herein by reference.

Examples of pro-drugs are as follows. An in vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$–$C_6$alkoxymethyl esters for example methoxymethyl, $C_1$–$C_6$alkanoyloxymethyl esters for example pivaloyloxymethyl, phthalidyl esters, $C_3$–$C_8$cycloalkoxycarbonyloxy$C_1$–$C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in vivo hydrolysable ester of a compound of the invention containing a hydroxy group includes inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

A further feature of the invention is a pharmaceutical composition comprising a compound of formula (I) as defined above, or a salt, solvate or prodrug thereof, together with a pharmaceutically-acceptable diluent or carrier.

According to another aspect of the invention there is provided a compound of formula (I) as defined above for use as a medicament.

Further according to the invention there is provided a compound of formula (I) for use in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of formula (I), or salt, solvate or pro-drug thereof, to a mammal in need of such treatment.

Specific disease which may be treated by the compound or composition of the invention include: blood glucose lowering in diabetes mellitus type 2 without a serious risk of hypoglycaemia (and potential to treat type 1), dyslipidemea, obesity, insulin resistance, metabolic syndrome X, impaired glucose tolerance.

As discussed above, thus the GLK/GLKRP system can be described as a potential "diabesity" target (of benefit in both diabetes and obesity). Thus, according to another aspect of the invention there if provided the use of a compound of formula (I), or salt, solvate or pro-drug thereof, in the preparation of a medicament for use in the combined treatment or prevention of diabetes and obesity.

According to another aspect of the invention there if provided the use of a compound of formula (I), or salt, solvate or pro-drug thereof, in the preparation of a medicament for use in the treatment or prevention of obesity.

According to a further aspect of the invention there is provided a method for the combined treatment of obesity and diabetes by administering an effective amount of a compound of formula (I), or salt, solvate or pro-drug thereof, to a mammal in need of such treatment.

According to a further aspect of the invention there is provided a method for the treatment of obesity by administering an effective amount of a compound of formula (I), or salt, solvate or pro-drug thereof, to a mammal in need of such treatment.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:

1) Insulin and insulin analogues;
2) Insulin secretagogues including sulphonylureas (for example glibenclamide, glipizide) and prandial glucose regulators (for example repaglinide, nateglinide);
3) Insulin sensitising agents including PPARg agonists (for example pioglitazone and rosiglitazone);
4) Agents that suppress hepatic glucose output (for example metformin).
5) Agents designed to reduce the absorption of glucose from the intestine (for example acarbose);
6) Agents designed to treat the complications of prolonged hyperglycaemia;
7) Anti-obesity agents (for example sibutramine and orlistat);
8) Anti-dyslipidaemia agents such as, HMG-CoA reductase inhibitors (statins, e.g. pravastatin); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
9) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
11) Anti-inflammatory agents, such as non-steroidal anti-infammatory drugs (eg. aspirin) and steroidal anti-inflammatory agents (eg. cortisone).

According to another aspect of the present invention there is provided individual compounds produced as end products in the Examples set out below and salts, solvates and pro-drugs thereof.

Another aspect of the present invention provides a process for preparing a compound of formula (I) or a salt, solvate or pro-drug thereof which process (wherein variable groups are, unless otherwise specified, as defined in formula (I)) comprises:

Process 1): reacting an acid of formula (IIa) or (IIb):

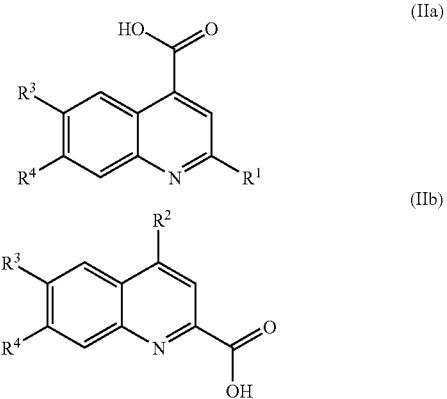

or an activated derivative thereof; with a compound of formula (III):

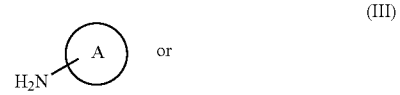

Process 2) for compounds of formula (I) wherein $R^6$ is carboxy; deprotecting a compound of formula (IIIa) or (IIIb):

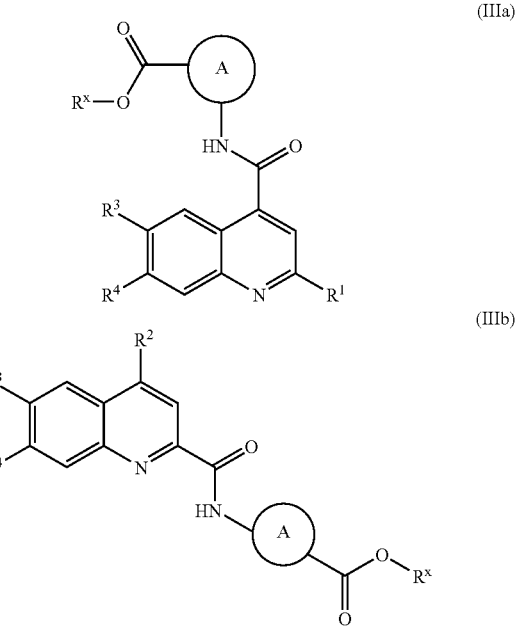

wherein $R^xOC(O)$— is an ester group;

and thereafter if necessary or desirable:
i) converting a compound of the formula (I) into another compound of the formula (I);
ii) removing any protecting groups;
iii) forming a salt, solvate or pro-drug thereof.

Suitable activated acid derivatives include acid halides, for example acid chlorides, and active esters, for example pentafluorophenyl esters. The reaction of these types of compounds with amines is well known in the art.

The group $R^xOC(O)$— is an ester. Suitable values for $R^x$ are $C_{1-6}$alkyl and benzyl, particularly methyl and ethyl.

The reactions described above may be performed under standard conditions. The intermediates described above are commercially available, are known in the art or may be prepared by known procedures.

Some of the intermediates described herein are novel and are thus provided as a further feature of the invention. For example compounds of formula (IIIa) and (IIIb) are provided as a further feature of the invention.

During the preparation process, it may be advantageous to use a protecting group. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms). Examples of carboxy protecting groups include straight or branched chain $C_{1-12}$alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri (lower alkyl)silyl groups (e.g. trimethylsilyl and t-butyldimethylsilyl); tri(lower alkyl)silyl lower alkyl groups (e.g. trimethylsilylethyl); and $C_{2-6}$alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, acid-, base, metal- or enzymically-catalysed hydrolysis, or photolytically for groups such as o-nitrobenzyloxycarbonyl, or with fluoride ions for silyl groups.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

BIOLOGICAL

Tests:

The biological effects of the compounds of formula (I) may be tested in the following way:

(1) Enzymatic activity of GLK may be measured by incubating GLK, ATP and glucose. The rate of product formation may be determined by coupling the assay to a G-6-P dehydrogenase, NADP/NADPH system and measuring the increase in optical density at 340 nm (Matschinsky et al 1993).

(2) A GLK/GLKRP binding assay for measuring the binding interactions between GLK and GLKRP. The method may be used to identify compounds which modulate GLK by modulating the interaction between GLK and GLKRP. GLKRP and GLK are incubated with an inhibitory concentration of F-6-P, optionally in the presence of test compound, and the extent of interaction between GLK and GLKRP is measured. Compounds which either displace P-6-P or in some other way reduce the GLK/GLKRP interaction will be detected by a decrease in the amount of GLK/GLKRP complex formed. Compounds which promote F-6-P binding or in some other way enhance the GLK/GLKRP interaction will be detected by an increase in the amount of GLK/GLKRP complex formed. A specific example of such a binding assay is described below GLK/GLKRP Scintillation Proximity Assay Compounds of the invention were found to have an activity of less than 10 μm when tested in the GLK/GLKRP scintillation proximity assay described below.

Recombinant human GLK and GLKRP were used to develop a "mix and measure" 96 well SPA (scintillation proximity assay) as described in WO01/20327 (the contents of which are incorporated herein by reference). GLK (Biotinylated) and GLKRP are incubated with streptavidin linked SPA beads (Amersham) in the presence of an inhibitory concentration of radiolabelled [3H]F-6-P (Amersham Custom Synthesis TRQ8689), giving a signal. Compounds which either displace the F-6-P or in some other way disrupt the GLK/GLKRP binding interaction will cause this signal to be lost.

Binding assays were performed at room temperature for 2 hours. The reaction mixtures contained 50 mM Tris-HCl (pH 7.5), 2 mM ATP, 5 mM $MgCl_2$, 0.5 mM DTT, recombinant biotinylated GLK (0.1 mg), recombinant GLKRP (0.1 mg), 0.05 mCi [3H] F-6-P (Amersham) to give a final volume of 100 ml. Following incubation, the extent of GLK/GLKRP complex formation was determined by addition of 0.1 mg/well avidin linked SPA beads (Amersham) and scintillation counting on a Packard TopCount NXT.

(3) A F-6-P/GLKRP binding assay for measuring the binding interaction between GLKRP and F-6-P. This method may be used to provide further information on the mechanism of action of the compounds. Compounds identified in the GLK/GLKRP binding assay may modulate the interaction of GLK and GLKRP either by displacing F-6-P or by modifying the GLK/GLKRP interaction in some other way. For example, protein-protein interactions are generally known to occur by interactions through multiple binding sites. It is thus possible that a compound which modifies the interaction between GLK and GLKRP could act by binding to one or more of several different binding sites.

The F-6-P/GLKRP binding assay identifies only those compounds which modulate the interaction of GLK and GLKRP by displacing F-6-P from its binding site on GLKRP.

GLKRP is incubated with test compound and an inhibitory concentration of F-6-P, in the absence of GLK, and the extent of interaction between F-6-P and GLKRP is measured. Compounds which displace the binding of F-6-P to GLKRP may be detected by a change in the amount of GLKRP/F-6-P complex formed. A specific example of such a binding assay is described below F-6-P/GLKRP Scintillation Proximity Assay Recombinant human GLKRP was used to develop a "mix and measure" 96 well scintillation proximity assay) as described in WO01/20327 (the contents of which are incorporated herein by reference). FLAG-tagged GLKRP is incubated with protein A coated SPA beads (Amersham) and an anti-FLAG antibody in the presence of an inhibitory concentration of radiolabelled [3H]F-6-P. A signal is generated. Compounds which displace the F-6-P will cause this signal to be lost. A combination of this assay and the GLK/GLKRP binding assay will allow the observer to identify compounds which disrupt the GLK/GLKRP binding interaction by displacing F-6-P.

Binding assays were performed at room temperature for 2 hours. The reaction mixtures contained 50 mM Tris-HCl (pH 7.5), 2 mM ATP, 5 mM $MgCl_2$, 0.5 mM DTT, recombinant FLAG tagged GLKRP (0.1 mg), Anti-Flag M2 Antibody (0.2mg) (IBI Kodak), 0.05 mCi [3H] F-6-P (Amersham) to give a final volume of 100 ml. Following incubation, the extent of F-6-P/GLKRP complex formation was determined by addition of 0.1 mg/well protein A linked SPA beads (Amersham) and scintillation counting on a Packard TopCount NXT.

Production of Recombinant GLK and GLKRP:

Preparation of mRNA

Human liver total mRNA was prepared by polytron homogenisation in 4M guanidine isothiocyanate, 2.5 mM citrate, 0.5% Sarkosyl, 100 mM b-mercaptoethanol, followed by centrifugation through 5.7M CsCl, 25 mM sodium acetate at 135,000 g (max) as described in Sambrook J, Fritsch EF & Maniatis T, 1989.

Poly $A^+$ mRNA was prepared directly using a FastTrack™ mRNA isolation kit (Invitrogen).

PCR Amplification of GLK and GLKRP cDNA Sequences

Human GLK and GLKRP cDNA was obtained by PCR from human hepatic mRNA using established techniques described in Sambrook, Fritsch & Maniatis, 1989. PCR primers were designed according to the GLK and GLKRP cDNA sequences shown in Tanizawa et al 1991 and Bonthron, D. T. et al 1994 (later corrected in Warner, J. P. 1995).

Cloning in Bluescript II Vectors

GLK and GLKRP cDNA was cloned in E. coli using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

E. Coli transformations were generally carried out by electroporation. 400 ml cultures of strains DH5a or BL21 (DE3) were grown in L-broth to an OD 600 of 0.5 and harvested by centrifugation at 2,000 g. The cells were washed twice in ice-cold deionised water, resuspended in 1 ml 10% glycerol and stored in aliquots at −70° C. Ligation mixes were desalted using Millipore V series™ membranes (0.0025 mm) pore size). 40 ml of cells were incubated with 1 ml of ligation mix or plasmid DNA on ice for 10 minutes in 0.2 cm electroporation cuvettes, and then pulsed using a Gene Pulser™ apparatus (BioRad) at 0.5 $kVcm^{-1}$, 250 mF, 250. Transformants were selected on L-agar supplemented with tetracyline at 10 mg/ml or ampicillin at 100 mg/ml.

Expression

GLK was expressed from the vector pTB375NBSE in E. coli BL21 cells, producing a recombinant protein containing a 6-His tag immediately adjacent to the N-terminal methionine. Alternatively, another suitable vector is pET21(+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in E. coli BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

Biotinylation of GLK:

GLK was biotinylated by reaction with biotinamidocaproate N-hydroxysuccinimide ester (biotin-NHS) purchased from Sigma-Aldrich (cat no. B2643). Briefly, free amino groups of the target protein (GLK) are reacted with biotin-NHS at a defined molar ratio forming stable amide bonds resulting in a product containing covalently bound biotin. Excess, non-conjugated biotin-NHS is removed from the product by dialysis. Specifically, 7.5 mg of GLK was added to 0.31 mg of biotin-NHS in 4 mL of 25 mM HERPES pH 7.3, 0.15 M KCl, 1 mM dithiothreitol, 1 mM EDTA, 1 mM $MgCl_2$ (buffer A). This reaction mixture was dialysed against 100 mL of buffer A containing a further 22 mg of biotin-NHS. After 4 hours excess biotin-NHS was removed by extensive dialysis against buffer A.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation in vacuo and work-up procedures were carried out after removal of residual solids such as drying agents by filtration;

(ii) operations were carried out at room temperature, that is in the range 18–25° C. and under an atmosphere of an inert gas such as argon or nitrogen;

(iii) yields are given for illustration only and are not necessarily the maximum attainable;

(iv) the structures of the end-products of the formula (I) were confirmed by nuclear (generally proton) magnetic resonance (NMR) and mass spectral techniques; proton magnetic resonance chemical shift values were measured on the delta scale in deuterated dimethyl sulphoxide unless otherwise stated, and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Silica gel 60, 0.040–0.063 mm, 230–400 mesh); and (vi) the following abbreviations are used:

DMF dimethylformamide; and

THF tetrahydrofuran.

EXAMPLE 1

2-(2-Chlorobenzyloxy)-4-[N-(5-carboxythiazol-2-yl) carbamoyl]-6-methylquinoline

Sodium hydroxide solution (0.3 ml of 2M, 0.6 mmol) was added to a stirred suspension of 2-(2-chlorobenzyloxy)-4-[N-(5-ethoxycarbonylthiazol-2-yl)carbamoyl]-6-methylquinoline (Method 1; 0.097 g, 0.202 mmol) in THF (5 ml) and water (2 ml), and the reaction mixture stirred at ambient temperature for 4 hrs. The reaction mixture was adjusted to pH 4–5 with aqueous hydrochloric acid (1M), and concentrated in vacuo. The solid thus precipitated was filtered, washed with water and dried to give the title compound as a colourless solid (0.030 g, 33%). NMR: 2.45 (3H, s), 5.60 (2H, s), 7.40 (3H, m), 7.50 (1H, m), 7.60 (1H, d), 7.65 (1H, m), 7.80 (2H, t), 7.90 (1H, d), 8.15 (1H, s); m/z

EXAMPLES 2–6

The following compounds were prepared by the procedure of Example 1 using the appropriate starting materials.

| No | Structure | NMR | MS | SM |
|---|---|---|---|---|
| 2[1] | 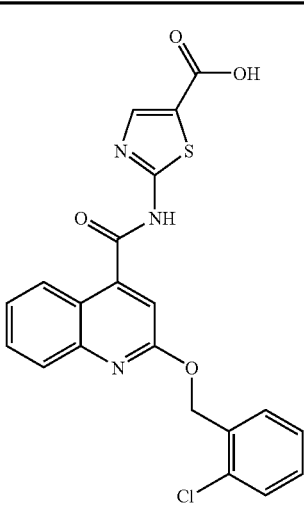 | 5.60(2H, s), 7.19(2H, m), 7.25(1H, s), 7.55(2H, m), 7.65(1H, m), 7.75(1H, t), 7.90(1H, d), 8.00(1H, d), 8.15(1H, s) | 440 438 | Method 2 |

-continued
| No | Structure | NMR | MS | SM |
|---|---|---|---|---|
| 3 | 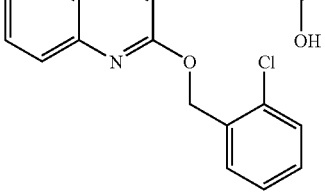 | 2.40(3H s), 5.60(2H, s), 7.30(1H, s), 7.40 (2H, m), 7.55(2H, m), 7.65(1H, m), 7.75 (2H, m), 8.40(2H, m), 8.85(1H, s) | 448 446 | Method 3 |
| 4 | 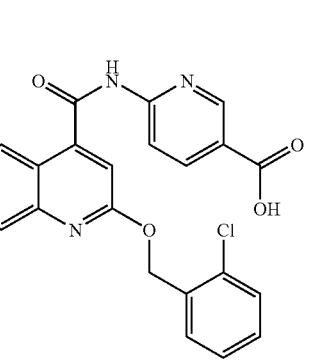 | 5.60(2H, s), 7.40(3H, m), 7.50(2H, m), 7.70(2H, m), 7.90(1H, d), 8.00(1H, d), 8.40(2H, m), 8.85(1H, s) | 434 432 | Method 4 |
| 5 | 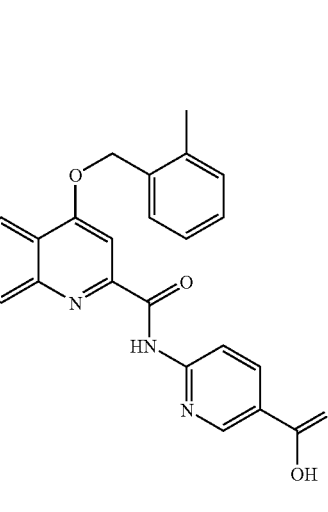 | 2.40(3H, s), 5.55(2H, s), 7.25(3H, m), 7.55(1H, br d), 7.70(1H, q), 7.90(2H, m), 8.20(2H, d), 8.40(2H, s), 8.90(1H, s) | 414 412 | Method 5 |
| 6 | 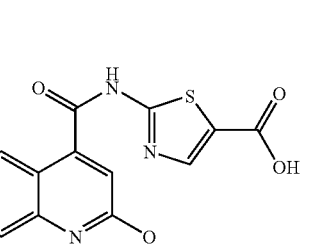 | 0.95(3H, t), 1.35(3H, d), 1.70(2H, m), 5.35(1H, q), 7.25(1H, s), 7.45(1H, t), 7.70(1H, t), 7.80(1H, d), 8.00(1H, d), 8.05(1H, s) | 372 370 | Method 6 |
[1]The reaction mixture was heated with stirring at 57° C. until LC-MS indicated that reaction was complete.

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1

2-(2-Chlorobenzyloxy)-4-[N-(5-ethoxycarbonylthiazol-2-yl)carbamoyl]-6-methylquinoline To a stirred solution of 2-(2-chlorobenzyloxy)-4-carboxy-6-methylquinoline (Method 7; 0.350 g, 1.067 mmol) and ethyl 2-aminothiazole-5-carboxylate (0.184 g, 1.067 mmol) in dimethyl formamide (DMF, 6 ml) was added 1-(3-dimethylaminopropyl)-3-ethyl-carbodiimide hydrochloride (0.307 g, 1.601 mmol) and 4-dimethylaminopyridine (0.391 g, 3.202 mmol). The reaction mixture was stirred overnight at room temperature, and then diluted with ethyl acetate (20 ml). The mixture was washed with water (20 ml), and the aqueous washings extracted with ethyl acetate (3×15 ml); the organic phases were combined and concentrated in vacuo. Flash chromatography on silica gel, eluting with a gradient of 2–20% ethyl acetate in iso-hexane, gave the title compound as a colourless solid (0.100 g, 19%). NMR: 1.30 (3H, t), 2.40 (3H, s), 4.30 (2H, q), 6.65 (2H, d), 7.20 (2H, m), 7.55 (2H, m), 7.65 (1H, m), 7.75 (1H, d), 7.95 (1H, s), 8.10 (2H, m), 8.15 (1H, s); m/z 482 (M+H)$^+$, 480 (M−H)$^+$,

Methods 2–6

The following compounds were prepared by the procedure of Method 1.

| Method | Compound | SM |
| --- | --- | --- |
| 2 | 2-(2-Chlorobenzyloxy)-4-[N-(5-ethoxycarbonylthiazol-2-yl)carbamoyl]quinoline | Method 8 |
| 3 | 2-(2-Chlorobenzyloxy)-4-[N-(5-methoxypyridin-2-yl)carbamoyl]-6-methylquinoline | Method 7 |
| 4 | 2-(2-Chlorobenzyloxy)-4-[N-(5-methoxypyridin-2-yl)carbamoyl]quinoline | Method 8 |
| 5 | 2-[N-(5-Methoxypyridin-2-yl)carbamoyl]-4-(2-methylbenzyoxy)quinoline | Method 9 |
| 6 | 2-(sec-Butoxy)-4-[N-(5-methoxycarbonylthiazol-2-yl)carbamoyl]quinoline | Method 10 |

Method 7

2-(2-Chlorobenzyloxy)4-carboxy-6-methylquinoline

To 2-(2-chlorobenzyloxy)-4-(2-chlorobenzyloxycarbonyl)-6-methylquinoline (Method 11; 0.980 g, 2.173 mmol) in THF (100 ml) was added a solution of sodium hydroxide (261 mg, 6.519 mmol) in water (2.6 ml) followed by water (60 ml) and methanol (10 ml). The reaction mixture was stirred at ambient temperature for 2 hrs 30 min and then adjusted to pH 4–5 with 1M HCl. It was then concentrated in vacuo and the resulting solid filtered, washed with water, and dried to give the title compound as a colourless solid (0.704 g, 99%). NMR: 2.45 (3H, s), 5.60 (2H, s), 7.35 (3H, m), 7.50 (1H, m), 7.55 (1H, dd), 7.65 (1H, m), 7.75 (1H, d), 8.30 (1H, s); m/z 328 (M+H)$^+$, 326 (M−H)$^−$.

Methods 8–10

The following compounds were prepared by the procedure of Method 7.

| Method | Compound | SM |
| --- | --- | --- |
| 8 | 2-(2-Chlorobenzyloxy)-4-carboxyquinoline | Method 12 |
| 9 | 2-Carboxy-4-(2-methylbenzyoxy)quinoline | Method 13 |
| 10 | 2-(sec-Butoxy)-4-carboxyquinoline | Method 14 |

Method 11

2-(2-Chlorobenzyloxy)-4-(2-chlorobenzyloxycarbonyl)-6-methylquinoline

To a solution of 2-hydroxy-6-methyl quinoline4-carboxylic acid (0.757 g, 3.731 mmol), triphenyl phosphine (2.940 g, 11.208 mmol) and 2-chlorobenzyl alcohol (1.060 g, 7.433 mmol) in THF (30 ml) was added dropwise di-isopropyl azodicarboxylate (2.20 ml, 11.19 mmol). The reaction was stirred at ambient temperature for 72 hrs and then concentrated in vacuo. The residue was chromatographed on silica gel, eluting with a gradient of 0–100% ethyl acetate in iso-hexane to give the title compound as an off white solid (1.080 g, 64%). NMR: 2.45 (3H, s), 5.55 (2H, s), 5.60 (2H, s), 7.50 (10H, m), 7.80 (1H, d), 8.20 (1H, s); m/z 452 (M+H)$^+$.

Methods 12–14

The following compounds were prepared by the procedure of Method 11.

| Method | Compound | NMR | M/z |
| --- | --- | --- | --- |
| 12 | 2-(2-Chlorobenzyloxy)-4-(2-chlorobenzyloxycarbonyl)quinoline | 5.55(2H, s), 5.60(2H, s), 7.40(4H, m), 7.55(4H, m), 7.65(2H, m), 7.75(1H, t), 7.90(1H, d), 8.45(1H, d) | 438(M+H)$^+$ |
| 13 | 2-(2-methylbenzyoxycarbonyl)-4-(2-methylbenzyoxy)quinoline | 2.38(3H, s), 2.39(3H, s), 5.45(2H, s), 5.50(2H, s), 7.20(6H, m), 7.45(1H, d), 7.50(1H, d), 7.65(1H, t), 7.70(1H, s), 7.80(1H, t), 8.10(1H, d), 8.20(1H, d) | 398(M+H)$^+$ 396(M−H)$^−$ |
| 14 | 2-(sec-Butoxy)-4-(sec-butoxycarbonyl)quinoline | 0.90(6H, m), 1.35(6H, m), 1.70(4H, m), 5.05(1H, m), 5.15(1H, m), 7.30(1H, s), 7.50(1H, m), 7.70(1H, m), 7.80(1H, d), 8.40(1H, d) | 302(M+H)$^+$ |

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

REFERENCES

1. Printz, R. L., Magnuson, M. A. and Granner, D. K. (1993) Annual Review of Nutrition 13, 463–96
2. DeFronzo, R. A. (1988) Diabetes 37, 667–87
3. Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697–702
4. Bell, G. I., Pillis, S. J., Weber, I. T. and Polonsky, K. S. (1996) Annual Review of Physiology 58, 171–86
5. Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755–61
6. Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240–6
7. Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226–30
8. Caro, J. F., Triester, S., Patel, V. K., Tapscott, E. B., Frazier, N. L. and Dohm, G. L. (1995) Hormone & Metabolic Research 27, 19–22
9. Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287–95
10. Shiota, M., Postic, C., Fujimoto, Y., Jetton, T. L., Dixon, K., Pan, D., Grimsby, J., Grippo, J. F., Magnuson, M. A. and Cherrington, A. D. (2001) Diabetes 50, 622–9

11 Ferre, T., Pujol, A., Riu, E., Bosch, F. and Valera, A. (1996) Proceedings of the National Academy of Sciences of the United States of America 93, 7225–30
12 Seoane, J., Barbera, A., Telemaque-Potts, S., Newgard, C. B. and Guinovart, J. J. (1999) Journal of Biological Chemistry 274, 31833–8
13 Moore, M. C., Davis, S. N., Mann, S. L. and Cherrington, A. D. (2001) Diabetes Care 24, 1882–7
14 Alvarez, E., Roncero, I., Chowen, J. A., Vazquez, P. and Blazquez, E. (2002) Journal of Neurochemistry 80, 45–53
15 Lynch, R. M., Tompkins, L. S., Brooks, H. L., Dunn-Meynell, A. A. and Levin, B. E. (2000) Diabetes 49, 693–700
16 Roncero, I., Alvarez, E., Vazquez, P. and Blazquez, E. (2000) Journal of Neurochemistry 74, 1848–57
17 Yang, X. J., Kow, L. M., Funabashi, T. and Mobbs, C. V. (1999) Diabetes 48, 1763–1772
18 Schuit, F. C., Huypens, P., Heimberg, H. and Pipeleers, D. G. (2001) Diabetes 50, 1–11
19 Levin, B. E. (2001) International Journal of Obesity 25
20 Alvarez, E., Roncero, I., Chowen, J. A., Thorens, B. and Blazquez, E. (1996) Journal of Neurochemistry 66, 920–7
21 Mobbs, C. V., Kow, L. M. and Yang, X. J. (2001) American Journal of Physiology-Endocrinology & Metabolism 281, E649–54
22 Levin, B. E., Dunn-Meynell, A. A. and Routh, V. H. (1999) American Journal of Physiology 276, R[1223–31]
23 Spanswick, D., Smith, M. A., Groppi, V. E., Logan, S. D. and Ashford, M. L. (1997) Nature 390, 521–5
24 Spanswick, D., Smith, M. A., Mirshamsi, S., Routh, V. H. and Ashford, M. L. (2000) Nature Neuroscience 3, 757–8
25 Levin, B. E. and Dunn-Meynell, A. A. (1997) Brain Research 776, 146–53
26 Levin, B. E., Govek, E. K. and Dunn-Meynell, A. A. (1998) Brain Research 808, 317–9
27 Levin, B. E., Brown, K. L. and Dunn-Meynell, A. A. (1996) Brain Research 739, 293–300
28 Rowe, I. C., Boden, P. R. and Ashford, M. L. (1996) Journal of Physiology 497, 365–77
29 Fujimoto, K., Sakata, T., Arase, K., Kurata, K., Okabe, Y. and Shiraishi, T. (1985) Life Sciences 37, 2475–82
30 Kurata, K., Fujimoto, K. and Sakata, T. (1989) Metabolism: Clinical & Experimental 38, 46–51
31 Kurata, K., Fujimoto, K., Sakata, T., Etou, H. and Fukagawa, K. (1986) Physiology & Behavior 37, 615–20

The invention claimed is:

1. A compound of formula (I) or a salt, solvate or pro-drug thereof:

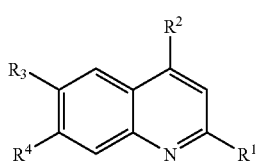

wherein:
one of $R^1$ and $R^2$ is a group (IA):

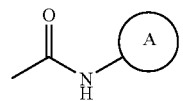

and the other $R^1$ and $R^2$ is $C_{1-4}$alkoxy optionally substituted on carbon by one or more groups selected from $R^5$;

Ring A is pyridin-2-yl or thiazol-2-yl; wherein said pyridin-2-yl or thiazol-2-yl is optionally substituted on carbon by one or more groups selected from $R^6$;

one of $R^3$ and $R^4$ is hydrogen and the other is selected from hydrogen, $C_{1-4}$alkyl, $C_{1-4}$alkoxy, carbocyclyl, heterocyclyl, carbocyclyloxy and heterocyclyloxy; wherein $R^3$ and $R^4$ are independently optionally substituted on carbon by one or more groups selected from $R^7$; and wherein if $R^3$ or $R^4$ is heterocyclyl, said heterocycyl contains an —NH— moiety, and the nitrogen of the —NH— moiety is optionally substituted by $C_{1-4}$alkyl;

$R^6$ is selected from halo, carboxy and $C_{1-4}$alkyl;

$R^5$ and $R^7$ are independently selected from halo, $C_{1-4}$alkyl, $C_{1-4}$alkoxy, N-($C_{1-4}$alkyl)amino, N,N-($C_{1-4}$alkyl)$_2$amino, carbocyclyl, heterocyclyl, carbocyclyloxy, heterocyclyloxy and carbocyclylidenyl; wherein $R^5$ and $R^7$ is independently optionally substituted on carbon by one or more groups selected from $R^8$; and wherein if $R^5$ and/or $R^7$ is heterocyclyl, said heterocyclyl contains an —NH— moiety, and the nitrogen of the —NH— moiety is optionally substituted by $C_{1-4}$alkyl; and $R^8$ is selected from halo, carboxy, methyl, ethyl, methoxy, ethoxy, methylamino, ethylamino, dimethylamino, diethylamino and N-methyl-N-ethylamino.

2. A compound according to claim 1 or a salt, solvate or pro-drug thereof, wherein Ring A in the group (IA) is substituted by carboxy and the $C_{1-4}$alkoxy group is substituted on carbon by one or more groups selected from $R^5$.

3. A compound according to claim 2 or a salt, solvate or pro-drug thereof, wherein $R^5$ is selected from carbocyclyl optionally substituted by one or more groups selected from $R^8$.

4. A compound according to claim 1 or a salt, solvate or pro-drug thereof, wherein one of $R^3$ and $R^4$ is hydrogen and the other is $C_{1-4}$alkyl.

5. A compound according to claim 1 or a salt. solvate or pro-drug thereof, selected from:
2-(2-Chlorobenzyloxy)-4-[N-5-carboxythiazol-2-yl)carbamoyl]-6-methylquinoline;
2-(2-Chlorobenzyloxy)-4-[N-5-carboxythiazol-2-yl)carbamoyl]-quinoline;
2-(2-Chlorobenzyloxy)-4-[N-5-carboxypyrid-2-yl)carbamoyl]-6-methylquinoline;
2-(2-Chlorobenzyloxy)-4-[N-5-carboxypyrid-2-yl)carbamoyl]-quinoline;
2-[N-5-carboxyprid-2-yl)carbamoyl]-4-(2-methylbenzyloxy)-quinoline; and
2-(1-methylpropoxy)-4-[N-(5-carboxythiazol-2-yl)carbamoyl]-quinoline.

6. A pharmaceutical composition comprising a compound according to any one of claims 1 and 2 to 5, or a salt, pro-drug or solvate thereof, together with a pharmaceutically acceptable diluent or carrier.

7. A process for preparing a compound of formula (I) or a salt, solvate or pro-drug thereof:

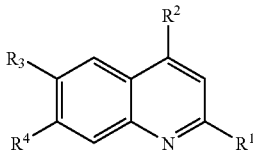

wherein:
one of $R^1$ and $R^2$ is a group (IA):

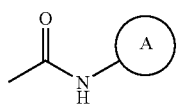

and the other $R^1$ and $R^2$ is $C_{1-4}$alkoxy optionally substituted on carbon by one or more groups selected from $R^5$;
Ring A is pyridin-2-yl or thiazol-2-yl; wherein said pyridin-2-yl or thiazol-2-yl is optionally substituted on carbon by one or more groups selected from $R^6$;
one of $R^3$ and $R^4$ is hydrogen and the other is selected from hydrogen, $C_{1-4}$alkyl, $C_{1-4}$alkoxy, carbocyclyl, heterocyclyl, carbocyclyloxy and heterocyclyloxy; wherein $R^3$ and $R^4$ are independently optionally substituted on carbon by one or more groups selected from $R^7$; and wherein if $R^3$ or $R^4$ is heterocyclyl, said heterocyclyl contains an —NH— moiety, and the nitrogen of the —NH— is optionally substituted by $C_{1-4}$alkyl;
$R^6$ is selected from halo, carboxy and $C_{1-4}$alkyl;
$R^5$ and $R^7$ are independently selected from halo, $C_{1-4}$alkyl, $C_{1-4}$alkoxy, N-($C_{1-4}$alkyl)amino, N,N-($C_{1-4}$alkyl)$_2$amino, carbocyclyl, heterocyclyl, carbocyclyloxy, heterocyclyloxy and carbocyclylidenyl; wherein $R^5$ and $R^7$ are independently optionally substituted on carbon by one or more $R^8$; and wherein if $R^5$ and/or $R^7$ is heterocyclyl, said heterocyclyl contains an —NH— moiety, and the nitrogen is of the —NH— moiety is optionally substituted by $C_{1-4}$alkyl; and
$R^8$ is selected from halo, carboxy, methyl, ethyl, methoxy, ethoxy, methylamino, ethylamino, dimethylamino, diethylamino and N-methyl-N-ethylamino
which process comprises:
Process 1): reacting an acid of formula (IIa) or (IIb):

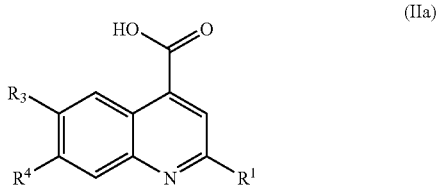

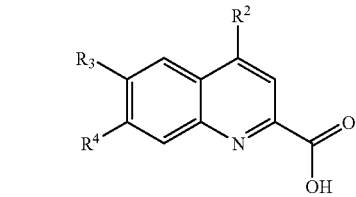

or an activated derivative thereof with a compound of formula (III)

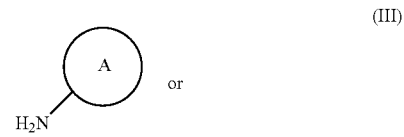

Process 2) for compounds of formula (I) wherein $R^6$ is carboxy; deprotecting a compound of formula (IIIa) or (IIIb):

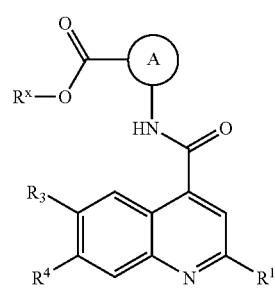

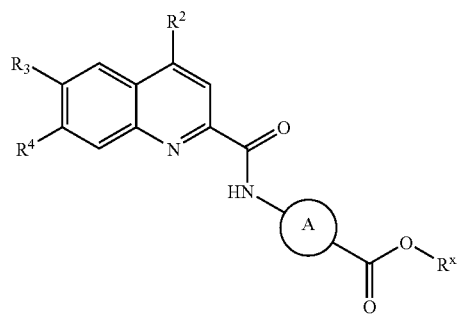

wherein $R^xOC(O)$— is an ester group and $R^x$ is selected from $C_{1-6}$alkyl and benzyl;
and thereafter optionally,
i) converting a compound of the formula (I) into another compound of the formula (I); and/or
ii) removing any protecting groups; and/or
iii) forming a salt, solvate or pro-drug thereof.

8. A compound of formula (IIIa) or a compound of formula (IIIb):

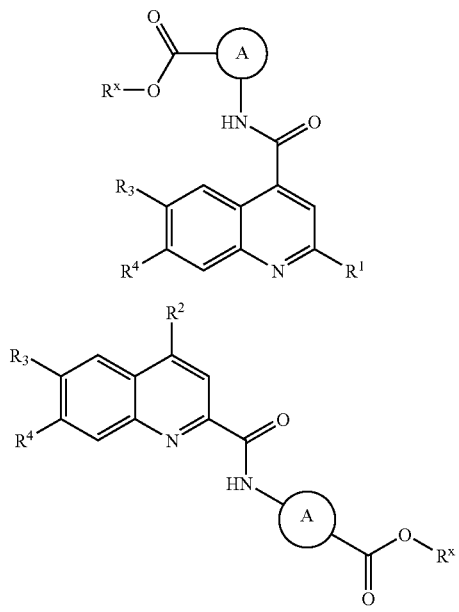

wherein R$^x$CO(O)— is an ester group and R$^x$ is selected from C$_{1-6}$alkyl and benzyl;

R$^1$ and R$^2$ are C$_{1-4}$alkoxy, optionally substituted on carbon by one or more groups selected from R$^5$;

Ring A is pyridin-2-yl or thiazol-2-yl: wherein said pyridin-2-yl or thiazol-2-yl is optionally substituted on carbon by one or more groups selected from R$^6$;

one of R$^3$ and R$^4$ is hydrogen and the other is selected from hydrogen, C$_{1-4}$alkyl, C$_{1-4}$alkoxy, carbocyclyl, heterocyclyl, carbocyclyloxy and heterocyclyloxy; wherein R$^3$ and R$^4$ are independently optionally substituted on carbon by one or more groups selected from R$^7$; and wherein if R$^3$ or R$^4$ is heterocyclyl, said heterocyclyl contains an —NH— moiety, and the nitrogen of the —NH— moiety is optionally substituted by C$_{1-4}$alkyl;

R$^6$ is selected from halo, carboxy and C$_{1-4}$alkyl;

R$^5$ and R$^7$ are independently selected from halo, C$_{1-4}$alkyl, C$_{1-4}$alkoxy, N-(C$_{1-4}$alkyl)amino, N,N-(C$_{1-4}$alkyl)$_2$amino, carbocyclyl, heterocyclyl, carbocyclyloxy, heterocyclyloxy and carbocyclylidenyl; wherein R$^5$ and R$^7$ is independently optionally substituted on carbon by one or more R$^8$; and wherein R$^5$ and/or R$^7$ is heterocyclyl, said heterocyclyl contains an —NH— moiety, and the nitrogen of the —NH— moiety is optionally substituted by C$_{1-4}$alkyl; and R$^8$ is selected from halo, carboxy, methyl, ethyl, methoxy, ethoxy, methylamino, ethylamino, dimethylamino, diethylamino and N-methyl-N-ethylamino.

9. The process of claim 7, wherein R$^x$ is selected from methyl and ethyl.

10. The compound of claim 8, wherein R$^x$ is selected from methyl and ethyl.

* * * * *